US00PP17991P2

(12) United States Plant Patent
Hoogendoorn

(10) Patent No.: US PP17,991 P2
(45) Date of Patent: Sep. 4, 2007

(54) ***ALSTROEMERIA* PLANT NAMED 'ZAPRIFABI'**

(50) Latin Name: *Alstroemeria hybrida*
Varietal Denomination: Zaprifabi

(75) Inventor: Cornelis Arie Hoogendoorn, Rijsenhout (NL)

(73) Assignee: Van Zanten Plants, B.V., Rijsenhout (NL)

( * ) Notice: Subject to any disclaimer, the term of this patent is extended or adjusted under 35 U.S.C. 154(b) by 0 days.

(21) Appl. No.: 11/255,219

(22) Filed: Oct. 20, 2005

(51) Int. Cl.
*A01H 5/00* (2006.01)

(52) U.S. Cl. ..... Plt./309
(58) Field of Classification Search ..... Plt./309
See application file for complete search history.

(56) References Cited

PUBLICATIONS

Upov–rom GTITM, Plant Variety Database, 2006/01, GTI Jouve Retrieval Software, Citation for *Alstroemeria* 'Zaprifabi' one page.*

Van Zanten Plants B.V. [online], [retieved on Nov. 15, 2006]. Retrieved form the Internet <http://www.royal-vanzanten.com/> 3 pages.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of *Alstroemeria* plant named 'Zaprifabi', characterized by its compact and mounded plant habit; vigorous growth habit; variegated dark green-colored foliage with white-colored margins; pale yellow-colored flowers; and good postproduction longevity.

1 Drawing Sheet

Botanical designation: *Alstroemeria hybrida.*
Cultivar denomination: 'Zaprifabi'.

BACKGROUND OF THE INVENTION

The present Invention relates to a new and distinct cultivar of *Alstroemeria* plant, botanically known as *Alstroemeria hybrida,* commercially used as a container *Alstroemeria,* and hereinafter referred to by the name 'Zaprifabi'.

The new *Alstroemeria* is a naturally-occurring branch mutation of the *Alstroemeria hybrida* cultivar Stapridani, disclosed in U.S. Plant Pat. No. 14,121. The new *Alstroemeria* was discovered and selected by the Inventor from a single plant within a population of plants of the cultivar Stapridani in a controlled environment in Rijsenhout, The Netherlands on May 2, 2002.

Asexual reproduction of the new cultivar by root divisions in a controlled environment in Rijsenhout, The Netherlands, since August, 2002, has shown that the unique features of this new *Alstroemeria* are stable and reproduced true to type in successive generations of asexual propagation.

SUMMARY OF THE INVENTION

Plants of the cultivar Zaprifabi have not been observed under all possible environmental conditions. The phenotype may vary somewhat with variations in environment such as temperature and light intensity without, however, any variance in genotype.

The following traits have been repeatedly observed and are determined to be the unique characteristics of 'Zaprifabi'. These characteristics in combination distinguish 'Zaprifabi' as a new and distinct cultivar:

1. Compact and mounded plant habit.
2. Vigorous growth habit.

3. Variegated dark green-colored foliage with white-colored margins.
4. Pale yellow-colored flowers.
5. Good postproduction longevity.

Plants of the new *Alstroemeria* can be compared to plants of the parent, the cultivar Stapridani. In side-by-side comparisons conducted in Rijsenhout, The Netherlands, plants of the new *Alstroemeria* differed from plants of the cultivar Stapridani primarily in leaf coloration as plants of the cultivar Stapridani did not have variegated foliage.

Plants of the new *Alstroemeria* can also be compared to plants of the cultivar Staprilene, disclosed in U.S. Plant Pat. No. 11,683. In side-by-side comparisons conducted in Rijsenhout, The Netherlands, plants of the new *Alstroemeria* differed from plants of the cultivar Staprilene in the following characteristics:

1. Plants of the new *Alstroemeria* were smaller than plants of the cultivar Staprilene.
2. Plants of the new *Alstroemeria* were more freely branching than plants of the cultivar Staprilene.
3. Plants of the new *Alstroemeria* had variegated foliage whereas plants of the cultivar Staprilene had solid green-colored foliage.
4. Plants of the new *Alstroemeria* had shorter leaves than plants of the cultivar Staprilene.
5. Plants of the new *Alstroemeria* and the cultivar Staprilene differed in flower coloration as plants of the cultivar Staprilene had white-colored flowers.

BRIEF DESCRIPTION OF THE PHOTOGRAPH

The accompanying colored photograph illustrates the overall appearance of the new *Alstroemeria,* showing the colors as true as it is reasonably possible to obtain in colored reproductions of this type. Colors in the photograph may differ slightly from the color values cited in the detailed botanical description which accurately describe the colors of the new *Alstroemeria*. The photograph comprises a side perspective view of a typical flowering plant of 'Zaprifabi' grown in a container.

DETAILED BOTANICAL DESCRIPTION

The aforementioned photograph and following observations and measurements describe plants of the new *Alstroemeria* grown in 17-cm containers in Rijsenhout, The Netherlands in a glass-covered greenhouse in ground beds. During the production of the plants, day temperatures ranged from 15° C. to 25° C., night temperatures ranged from 10° C. to 15° C. and light levels averaged 5,000 lux. Plants used for the photograph and description were about four months-old. The photograph and the description were taken in February, 2005. Color references are made to The Royal Horticultural Society Colour Chart, 1995 Edition, except where general terms of ordinary dictionary significance are used.

Botanical classification: *Alstroemeria hybrida* cultivar 'Zaprifabi'.

Parentage: Naturally-occurring branch mutation of the *Alstroemeria hybrida* cultivar Strapridani, disclosed in U.S. Plant Pat. No. 14,121.

Propagation:

*Type.*—By root divisions.

*Root description.*—Fibrous, fleshy, thick; white, close to 155D, in color.

*Rooting habit.*—Freely branching.

*Rhizomes.*—Shape: Elongate; rounded. Length: About 10 to 30 cm. Diameter: About 3 to 10 mm. Texture: Smooth. Color: Close to 155D.

Plant description:

*Plant habit.*—Compact and mounded growth habit; freely branching, bushy appearance. Vigorous growth habit.

*Plant height.*—About 15 cm to 25 cm.

*Plant diameter (spread).*—About 30 cm to 40 cm.

*Lateral stem description.*—Aspect: Mostly upright. Quantity per plant: About 15 to 20. Length: About 15 cm to 20 cm. Diameter: About 4 mm to 5 mm. Internode length: About 5 mm to 1.5 cm. Strength: Strong. Texture: Glabrous, smooth. Color: Close to 144B.

*Foliage description.*—Leaves asymmetrical; sessile. Length: About 7 cm to 8.5 cm. Width: About 2 cm to 2.5 cm. Shape: Lanceolate. Apex: Acute. Base: Attenuate. Margin: Entire. Texture, upper and lower surfaces: Smooth, glabrous. Venation pattern: Parallel. Color: Developing and fully developed foliage, upper surface: Close to 137B; at the margins, 157C; slightly glossy; venation, similar to lamina. Developing and fully developed foliage, lower surface: Close to 138B; at the margins, 157C; venation, similar to lamina.

Flower description:

*Flower type and habit.*—Single cup-shaped flowers arranged in compound umbels. Perianth segments separate. Freely and continuously flowering. Flowers not persistent.

*Natural flowering season.*—Flowering continuous during the spring in The Netherlands.

*Fragrance.*—None detected.

*Flower longevity on the plant.*—About four weeks.

*Flower buds.*—Length: About 3 cm to 4 cm. Diameter: About 1 cm to 1.5 cm. Shape: Roughly ovoid. Color: Close to 145A.

*Umbel length.*—About 9 cm to 11 cm.

*Umbel diameter.*—About 11 cm to 15 cm.

*Number of flowers per umbel.*—About 2 to 15.

*Flower length (height).*—About 6 cm to 8 cm.

*Flower diameter.*—About 6 cm to 7 cm.

*Flower depth.*—About 5 cm to 6 cm.

*Perianth.*—Arrangement: Six arranged in two whorls, each whorl with two lateral and one median segments. Outer perianth: Length, lateral segments: About 5.5 cm to 6 cm. Width, lateral segments: About 3 cm to 3.5 cm. Length, median segment: About 5.5 cm to 6 cm. Width, median segment: About 3 cm to 3.5 cm. Shape, lateral and median segments: Obovate. Apex, lateral and median segments: Emarginate with an apical tip. Base, lateral and median segments: Attenuate. Margin, lateral and median segments: Entire; weakly undulate. Texture, lateral and median segments: Smooth, glabrous; velvety. Color, lateral segments, when opening and fully opened, upper surface: 2D; apical tip, close to 144A; stripes, close to 59A. Color, lateral segments, when opening and fully opened, lower surface: 2D; apical tip, close to 144A. Color, median segment; when opening and fully opened, upper surface: 2D; apical tip, close to 144A; stripes, close to 59A. Color, median segment; when opening and fully opened, lower surface: 2D; towards the base, 73C; apical tip, close to 144A. Inner perianth: Length, lateral segments: About 5 cm to 6 cm. Width, lateral segments: About 1.5 cm to 2 cm. Length, median segment: About 5 cm to 5.5 cm. Width, median segment: About 1 cm to 1.5 cm. Shape, lateral and median segments: Oblanceolate. Apex, lateral and median segments: Acute. Base, lateral and median segments: Attenuate. Margin, lateral and median segments: Entire; weakly undulate. Texture, lateral and median segments: Smooth, glabrous; velvety. Color, lateral segments, when opening and fully opened, upper surface: 2D; towards the base, 2B; stripes, close to 59A. Color, lateral segments, when opening and fully opened, lower surface: 2D. Color, median segment; when opening and fully opened, upper surface: 2C; apical tip, close to 144A; stripes, close to 59A. Color, median segment; when opening and fully opened, lower surface: 2D; apical tip, close to 144A.

*Peduncles.*—Length: About 2 cm to 3 cm. Diameter: About 2 mm to 3 mm. Strength: Strong. Angle: About 20° to 40° from vertical. Texture: Smooth, glabrous. Color: Close to 144B.

*Pedicels.*—Length: About 1 cm to 1.5 cm. Diameter: About 1 mm to 2 mm. Strength: Strong. Angle: About 20° to 40° from vertical. Texture: Smooth, glabrous. Color: Close to 144B.

*Reproductive organs.*—Stamens: Quantity per flower: Six. Anther shape: Elliptical. Anther length: About 8 mm. Anther diameter: About 3 mm. Anther color: Close to 152B. Filament length: About 3.7 cm to 4.2 cm. Filament color: 27C. Pollen amount: Scarce. Pollen color: Brownish. Pistils: Quantity per flower: One. Style length: About 4 cm to 5 cm. Style color: 25C. Stigma color: 11C. Ovary color: Close to 144A.

*Fruit.*—Quantity of fruit per plant: Few. Shape: Globular. Color: 137D. Size: About 8 mm by 6 mm.

Disease/pest resistance: Plants of the new *Alstroemeria* have not been observed to be resistant to pathogens and pests common to *Alstroemerias*.

Temperature tolerance: Plants of the new *Alstroemeria* have been observed to tolerate temperatures from −5° C. to 40° C.

It is claimed:

1. A new and distinct cultivar of *Alstroemeria* plant named 'Zaprifabi', as illustrated and described.

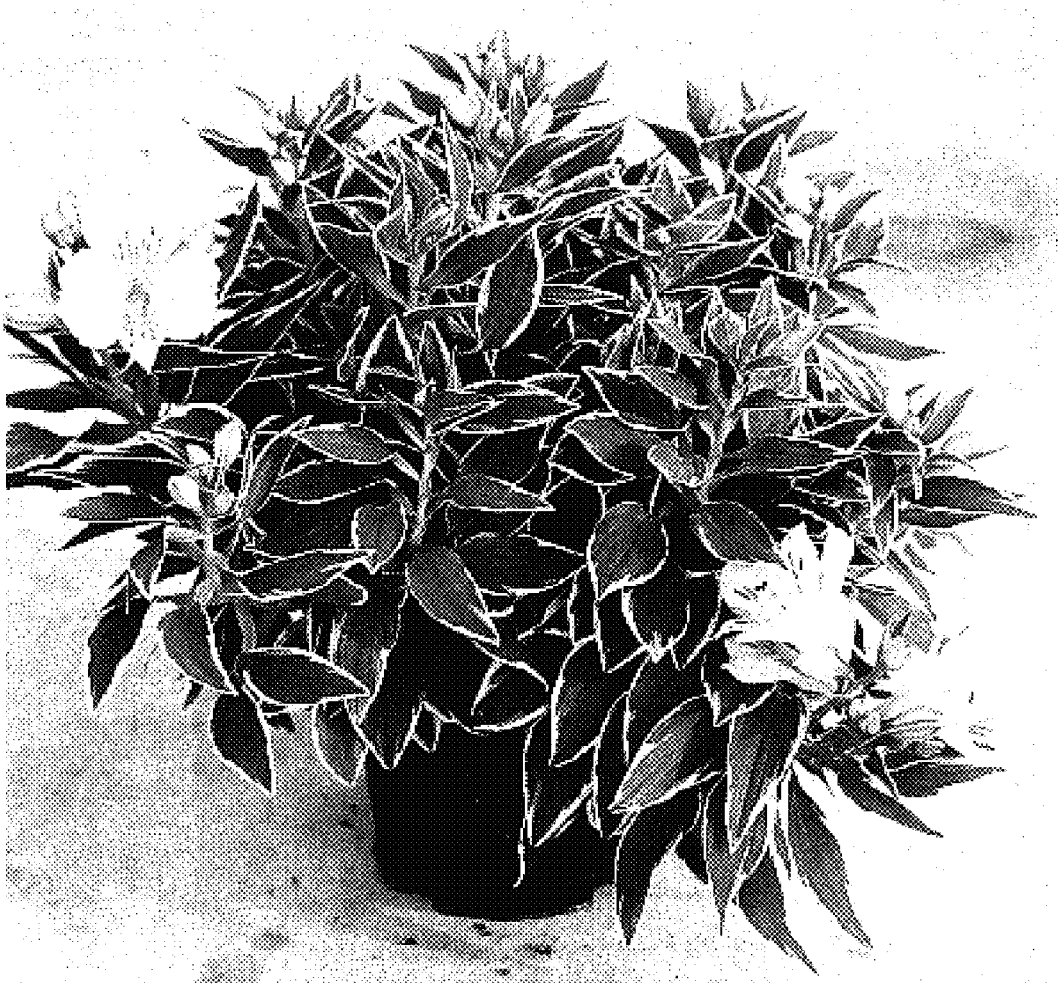

* * * * *